United States Patent
Schmand et al.

(10) Patent No.: US 8,410,776 B2
(45) Date of Patent: Apr. 2, 2013

(54) DETECTOR MODULE FOR AN EMISSION TOMOGRAPHY SCANNER

(75) Inventors: Matthias J. Schmand, Lenoir City, TN (US); Markus Vester, Nürnberg (DE); Nan Zhang, Knoxville, TN (US)

(73) Assignees: Siemens Medical Solutions USA, Inc., Malvern, PA (US); Siemens Aktiengesellschaft, Munich (DE)

( * ) Notice: Subject to any disclaimer, the term of this patent is extended or adjusted under 35 U.S.C. 154(b) by 856 days.

(21) Appl. No.: 12/585,867

(22) Filed: Sep. 28, 2009

(65) Prior Publication Data
US 2011/0074426 A1   Mar. 31, 2011

(51) Int. Cl.
*G01V 3/00* (2006.01)

(52) U.S. Cl. ......... 324/307; 324/316

(58) Field of Classification Search ......... 324/300–322; 600/407–445; 250/363, 366
See application file for complete search history.

(56) References Cited

U.S. PATENT DOCUMENTS

| | | | |
|---|---|---|---|
| 6,710,349 B2 * | 3/2004 | Shao | 250/363.03 |
| 7,759,647 B2 * | 7/2010 | Grazioso et al. | 250/363.05 |
| 2007/0102641 A1 * | 5/2007 | Schmand et al. | 250/363.03 |
| 2008/0135769 A1 * | 6/2008 | Rosen | 250/363.09 |

OTHER PUBLICATIONS

MR-PET:Combining Function,Anatomy, and More Schwaiger et al.; Others; 2005; DE.

* cited by examiner

*Primary Examiner* — Brij Shrivastav
(74) *Attorney, Agent, or Firm* — Harness, Dickey & Pierce, P.L.C.

(57) ABSTRACT

An emission tomography detector module and an emission tomography scanner are disclosed. In at least one embodiment, the emission tomography detector modules includes a scintillator to capture an photon, the scintillator emitting a scintillating light on capturing the photon; a first type of solid-state photodetector to detect the scintillating light; and a second type of solid-state photodetector to detect the scintillating light, wherein the first type of solid-state photodetector and the second type of solid-state photodetector are different with respect to a detecting property.

24 Claims, 6 Drawing Sheets

DETECTOR MODULE FOR AN EMISSION TOMOGRAPHY SCANNER

FIELD

At least one embodiment of the present invention generally relates to a detector module for an emission tomography scanner.

BACKGROUND

Nuclear medicine is a medical specialty, wherein radioactive decay is used to acquire images which show the function and anatomy of organs, bones or tissues of the body. Radiopharmaceuticals are introduced into the body, either by injection or ingestion, and concentrate in specific organs, bones or tissues of interest.

Such radiopharmaceuticals produce gamma photon emissions which emanate from the body and are captured by a scintillation crystal, with which the photons interact to produce flashes of light or "events." Events are detected by an array of photodetectors, such as photomultiplier tubes or photodiodes, and their spatial locations or positions are calculated and stored. In this way, an image of the organ or tissue under study is created from detection of the distribution of the radioisotopes in the body.

One particular nuclear medicine imaging technique is known as Emission Tomography. Emission tomography is used to produce images for diagnosing the biochemistry or physiology of a specific organ, tumor or other metabolically active site.

Two known types of emission tomography are a Positron Emission Tomography (PET) and a Single Photon Emission Computed Tomography (SPECT). For example, in a PET, measurement of the tissue concentration of a positron emitting radionuclide is based on coincidence detection of the two gamma photons arising from positron annihilation.

When a positron is annihilated by an electron, two 511 keV gamma photons are simultaneously produced and travel in approximately opposite directions. Gamma photons produced by an annihilation event can be detected by a pair of oppositely disposed radiation detectors capable of producing a signal in response to the interaction of the gamma photons with a scintillation crystal. Annihilation events are typically identified by a time coincidence between the detection of the two 511 keV gamma photons in the two oppositely disposed detectors, i.e., the gamma photon emissions are detected virtually simultaneously by each detector.

When two oppositely disposed gamma photons each strike an oppositely disposed detector to produce a time coincidence event, they also identify a line of coincidence or a line of response (LOR), along which the annihilation event has occurred. After being sorted into parallel projections, the LORs defined by the coincidence events are used to reconstruct a three-dimensional distribution of the positron-emitting radionuclide within the patient.

Emission tomography are particularly useful in obtaining images that reveal bioprocesses, e.g. the functioning of bodily organs such as the heart, brain, lungs, etc. and bodily tissues and structures such as the circulatory system.

On the other hand, Magnetic Resonance Imaging (MRI) is primarily used for obtaining high quality, high resolution anatomical and structural images of the body. MRI is based on the absorption and emission of energy in the radio frequency range primarily by the hydrogen nuclei of the atoms of the body. The major components of an MRI imager include a usually cylindrical magnet, gradient coils within the magnet, an RF coil within the gradient coil, and an RF shield that prevents the high power RF pulses from radiating outside of the MR imager, and keeps extraneous RF signals from being detected by the imager. A patient is placed on a patient bed or table within the magnet and is surrounded by the gradient and RF coils.

The magnet produces a $B_0$ magnetic field for the imaging procedure. The gradient coils produce a gradient in the $B_0$ field in the X, Y, and Z directions. The RF coil produces a $B_1$ magnetic field necessary to rotate the spins of the nuclei by 90° or 180°. The RF coil also detects the nuclear magnetic resonance signal from the spins within the body. A radio frequency source produces a sine wave of the desired frequency.

The concept of merging emission tomography and MR imaging modalities into a single device is generally known in the art. However, the photodetectors are either bulky or have limitations with respect to detection of a photon.

SUMMARY

In at least one embodiment of the invention, an emission tomography detector module is provided having at least one of a compact design and increased accuracy with respect to detection of a photon.

The first type of solid-state photodetector and the second type of solid-state photodetector having different detection properties enable in having a compact design and provide increased accuracy in detection of a photon.

According to an embodiment, the first type of solid-state photodetector and the second type of solid-state photodetector have different frequency response characteristics. For example, one of the solid-sate photodetectors may have a high frequency response characteristic and the other may have a low frequency response characteristic. This enables in increasing the energy resolution and timing resolution of the detector module.

According to yet another embodiment, the first type of solid-state photodetector is an avalanche photodiode. The avalanche photodiode has a low frequency response characteristic and thus, increases an energy resolution of the detector module.

According to yet another embodiment, the second type of solid-state photodetector is a silicon photomultiplier. The silicon photomultiplier has a high frequency response characteristic and thus, increases a timing resolution of the detector module.

Combining these two types of photodetectors provides a detector module with high energy resolution and timing resolution as the avalanche photodiode has high energy resolution and the silicon photomultiplier has high timing resolution.

According to yet another embodiment, the first type of solid-state photodetector and the second type of solid-state photodetector (24) are optically coupled to the scintillator. The photodetectors can be either directly coupled to the scintillator using a light guide. The photodetectors may even be indirectly optically coupled to the scintillator at a location distant from the scintillator block.

According to yet another embodiment, the detector module may further comprise a signal processing unit, the signal processing unit being operable to combine an output signal of the first type of solid-state photodetector and an output signal of the second type of solid-state photodetector to a combined output signal, the combined output signal being indicative for the photon captured by the scintillator. The signal processing unit provides a combined output indicative for the photon captured by the scintillator. Producing a combined output signal allows to generate a signal that reflects the advantages of both types of detectors, facilitating the correct detection of photons.

According to yet another embodiment, the output signal of the first type of solid-state photodetector may be used to discriminate photons based on their energy.

According to yet another embodiment, the output signal of the second type of solid-state photodetector is used for determining an incidence time of the photon.

According to yet another embodiment, the detector module may further comprise a plurality of first type of solid-state photodetectors arranged around the second type of solid-state photodetectors. This enables providing an Anger-mode lateral location within the detector module. The Anger-mode of the scintillator block 17 provides high spatial resolution and increase in the overall sensitivity of the scintillator block 17.

Another embodiment includes an emission tomography scanner comprising a pair of emission tomography detector modules, wherein each of the emission tomography detector modules comprise a scintillator to capture a photon, the scintillator emitting a scintillating light on capturing the photon, a first type of solid-state photodetector to detect the scintillating light, and a second type of solid-state photodetector to detect the scintillating light, wherein the first type of solid-state photodetector and the second type of solid-state photodetector are different with respect to a detecting property. The pair of detector modules enable in detecting a photon pair.

According to an embodiment, the emission tomography scanner may further comprise an evaluation unit to evaluate signals from the pair of detector modules, the evaluation unit being adapted to detect a coincidence event of a pair of photon. The coincidence event identifies a line of coincidence as the photons are oppositely disposed. The line of coincidence is a line connecting the two detector modules.

According to yet another embodiment, the evaluation unit may be adapted to determine a segment on a line of coincidence, the line of coincidence connecting the two detector modules, wherein the segment is determined using a time difference of incidence of a photon pair on the two detector modules. The segment enables in localizing the coincidence event to the segment on the line of coincidence. The detector used allows better performance in doing so, as it may discriminate photons based on their energy with a good quality due to the properties of the first type of solid-state photodetectors and as it may precisely determine the time of the photon event due to the properties of the second type of solid-state photodetectors.

Another embodiment includes a combined emission tomography and magnetic resonance imaging (MRI) apparatus, comprising an MRI scanner comprising a magnet system for generating a magnetic field for inducing nuclear magnetic resonance signals from nuclei of a subject to be imaged within a field of view of the MRI scanner, and an emission tomography detector module comprising a scintillator to capture a photon, the scintillator emitting a scintillating light on capturing the photon, a first type of solid-state photodetector to detect the scintillating light, and a second type of solid-state photodetector to detect the scintillating light, wherein the first type of solid-state photodetector and the second type of solid-state photodetector are different with respect to a detecting property.

BRIEF DESCRIPTION OF THE DRAWINGS

Embodiments of the present invention are further described hereinafter with reference to illustrated embodiments shown in the accompanying drawings, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details.

Figure 1:
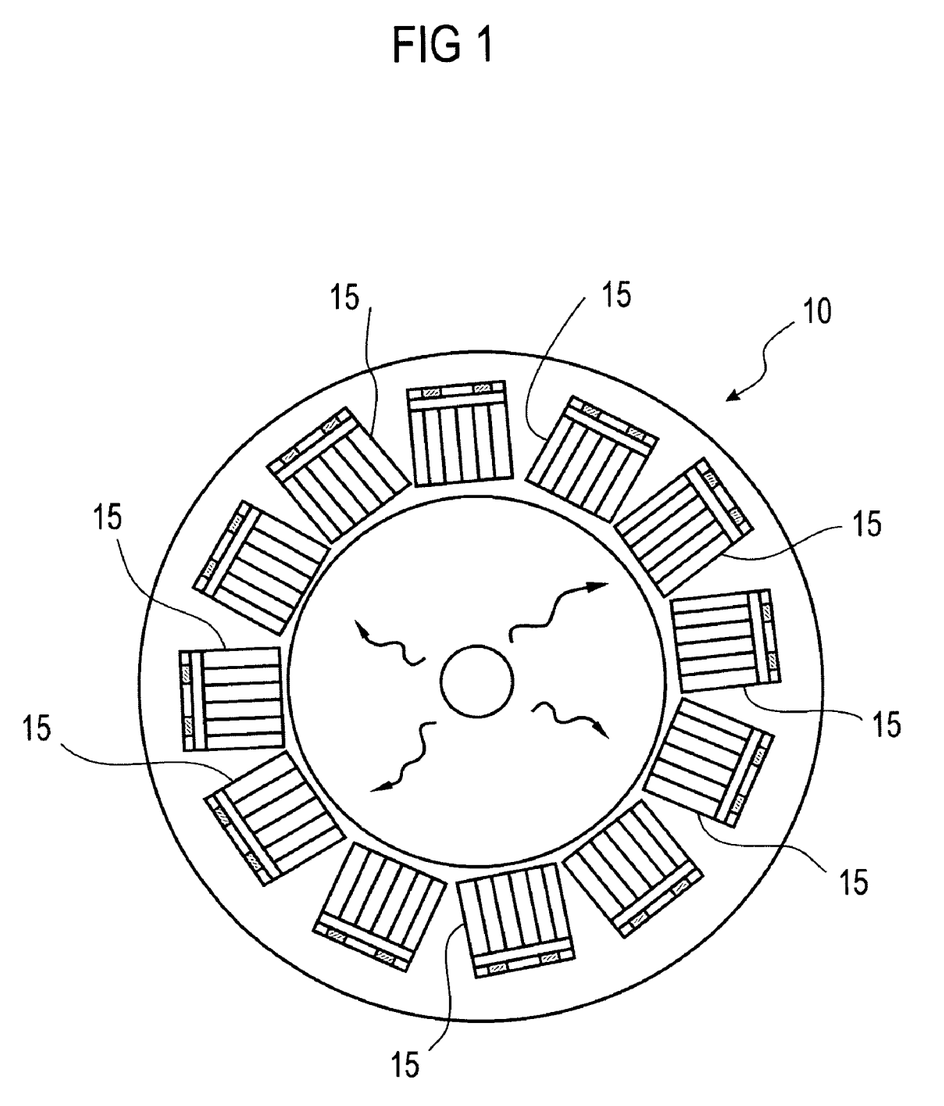
FIG. 1 illustrates a ring of an emission tomography scanner according to an embodiment herein.

Referring to FIG. 1, a ring 5 of an emission tomography scanner 10 in accordance with one embodiment of the invention includes a plurality of detector modules 15. In the shown example of FIG. 1, advantageously, the plurality of detector modules 15 are arranged on the ring 5 as a radius of the ring 5 is a constant. However, the detector modules 15 may be arranged in other geometrical configurations as desired.

Figure 2:
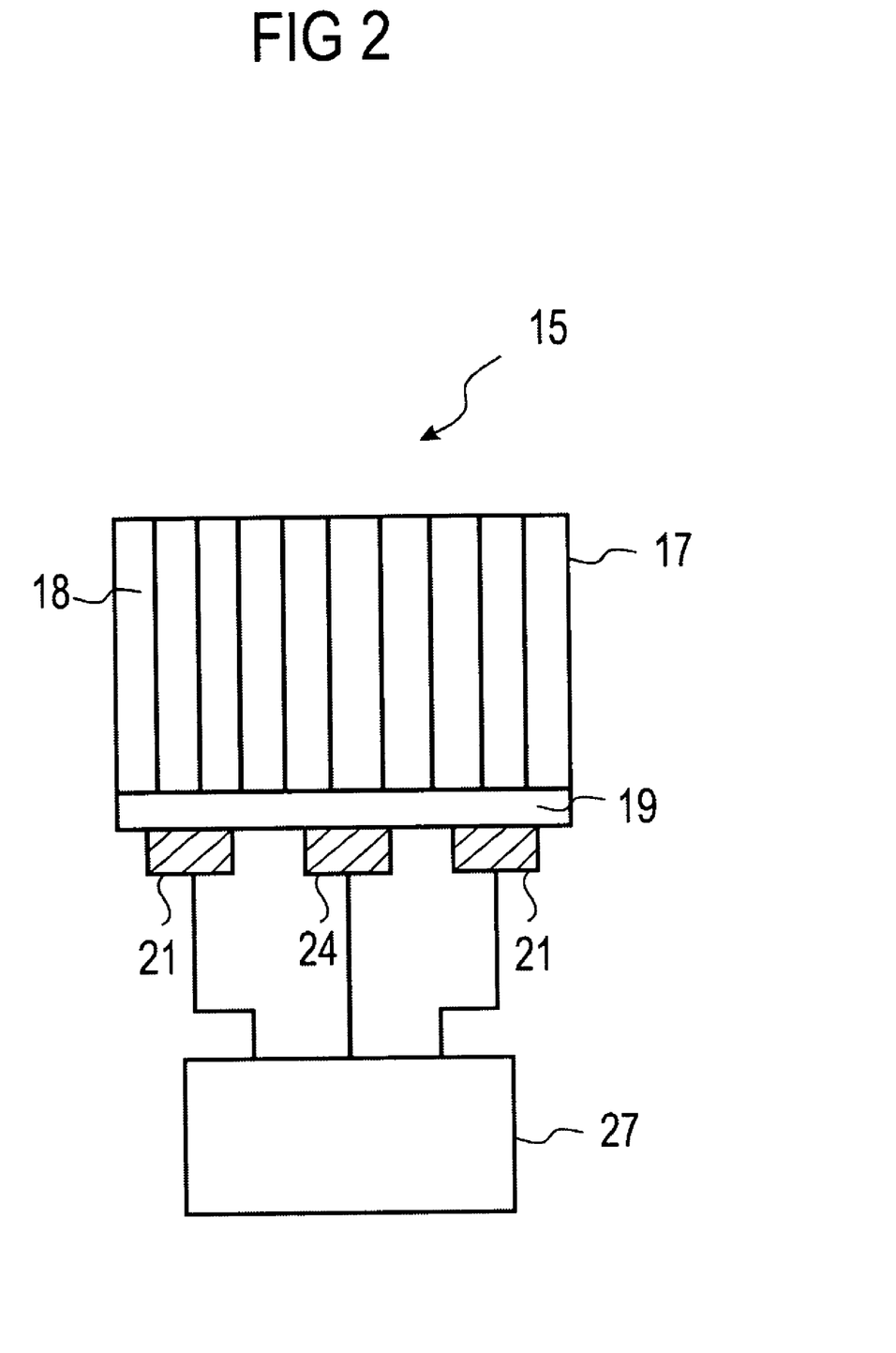
FIG. 2 illustrates a detector module for an emission tomography scanner according to an embodiment herein.

Referring now to FIG. 2, each detector module 15 includes a scintillator block 17 comprising a scintillator 18 that is optically coupled through a light guide 19 to a first type of solid-state photodetector 21 and a second type of solid-state photodetector 24. In the present example, it is shown that the first type of solid-state photodetector 21 and the second type of solid-state photodetector 24 are arranged on the scintillator block 17. However, the first type of solid-state photodetector 21 and the second type of solid-state photodetector 24 may not be directly arranged on the scintillator block 17. If the first type of solid-state photodetector 21 and the second type of solid-state photodetector 24 are not directly arranged on the scintillator block 17, then they may be optically coupled to the scintillator 18 using an optical fiber cable or other optical coupling means.

In accordance with an embodiment herein, the first and the second type of photodetectors 21, 24 are different with respect to a detecting property. For example, the first and the second type of photodetectors 21, 24 may differ with respect to a frequency response characteristic.

Having the first type and the second type of photodetectors 21, 24 being different with respect to the frequency response characteristic enable achieving increased energy resolution and timing resolution of the detector module. For example, the first type of the photodetector 21 may possess a low frequency response characteristic and the second type of photodetector 24 may possess a high frequency response characteristic. Alternatively, the first type of photodetector 21 may possess a low frequency response characteristic and the second type of photodetector 24 may possess a high frequency response characteristic. Thus, the first type of photodetector 21 possessing a low frequency response characteristic provide increased energy resolution of the detector module 15 and the second type of photodetector 24 possessing a high frequency response characteristic provide increased timing resolution of the detector module 15.

In an embodiment, the first type of photodetector may be an avalanche photodiode. The avalanche photodiode has a low frequency response characteristic. The second type of photodetector may be a silicon based photodetector, such as, a silicon photomultiplier and the like. The silicon multiplier has a high frequency response characteristic.

Referring still to FIG. 2, an output signal of the first type of solid-state photodetector 21 may be used to discriminate photons based on their energy as the first type of solid-state photodetector is of a low frequency response characteristic. An output signal of the second type of solid-state photodetector 24 may be used for determining an incidence time of the photons as the second type of solid-state photodetector is of a high frequency response characteristic. The output signal of the first type of photodetector is used for discriminating photons based on their energy.

In an embodiment herein, the output of the first type of solid-state photodetector 21 and the output of the second type of solid-state photodetector 24 may be provided to a signal processing unit 27. The signal processing unit 27 may combine the output of the first type of solid-state photodetector 21 and the output of the second type of solid-state photodetector 24 to produce a combined output signal. The combined output signal is an indicative for a photon captured by the scintillator 18. The combined output signal, from the scintillator block 17, enables in reducing the number of connections required for obtaining the output of the detector module 15. Moreover, producing a combined output signal facilitates the use of the detector module with the existing emission tomography scanners. Additionally, the signal processing unit 27 may be adapted to amplify and condition the combined output signal.

Figure 3:
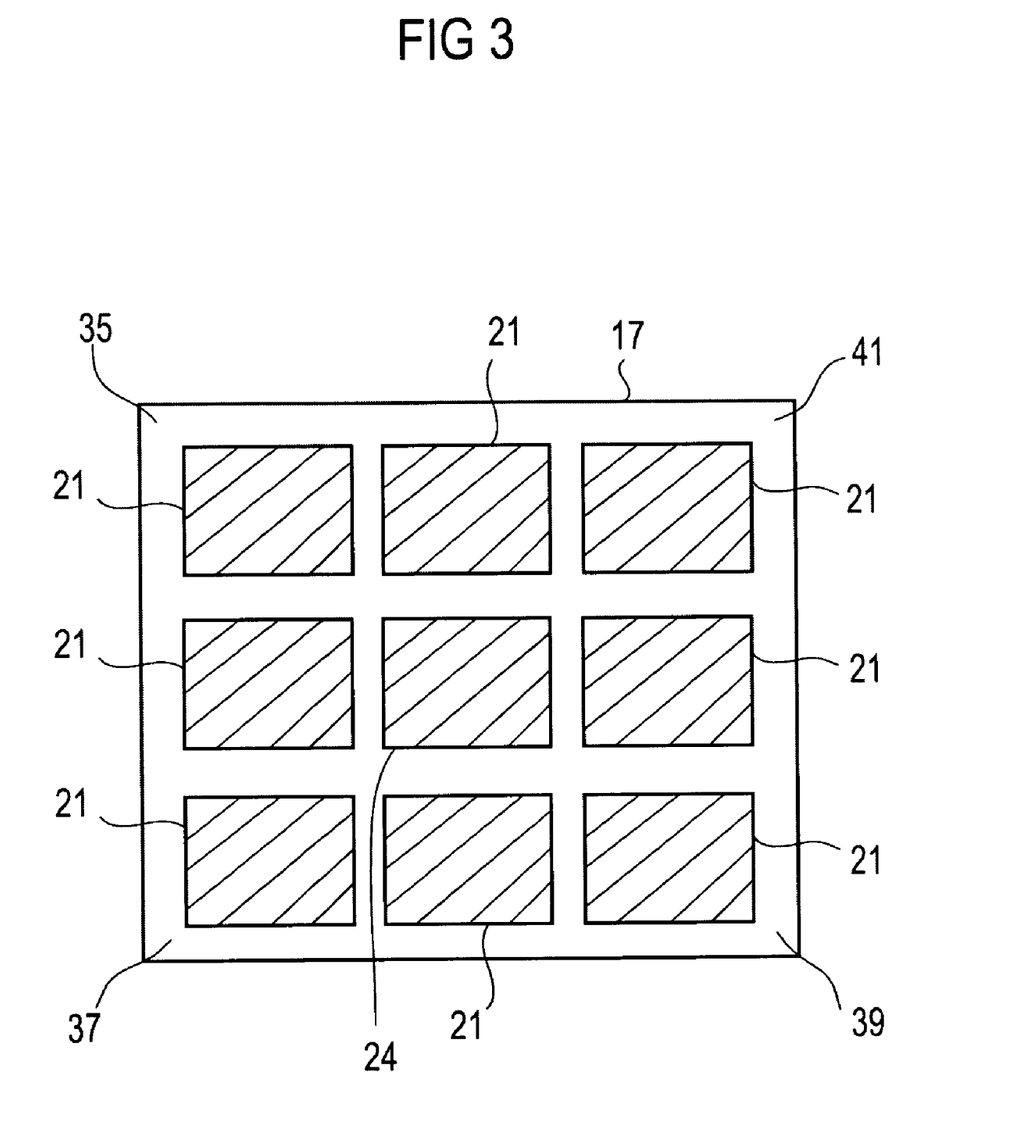
FIG. 3 illustrates a detector module according to a second embodiment.

Referring now to FIG. 3, in an embodiment, a plurality of the first type of solid-state photodetectors 21 may be arranged at the corners 35, 37, 39, 41 of the scintillator block 17. For an example, the first type of solid-state photodetectors 21 may be arranged on the scintillator block 17, such that, the first type of solid-state photodetectors 21 surround the second type of solid-state photodetector 24 substantially. However, it is not required that the first type of solid-state photodetectors 21 surround the second type of solid-state photodetectors 24 substantially. Providing a plurality of the first type of solid-state photodetectors 21 at the corners 35, 37, 39, 41 enable in achieving anger-mode lateral location within the scintillator block 17. The Anger-mode of the scintillator block 17 provides high spatial resolution and increase in the overall sensitivity of the scintillator block 17.

Figure 4:
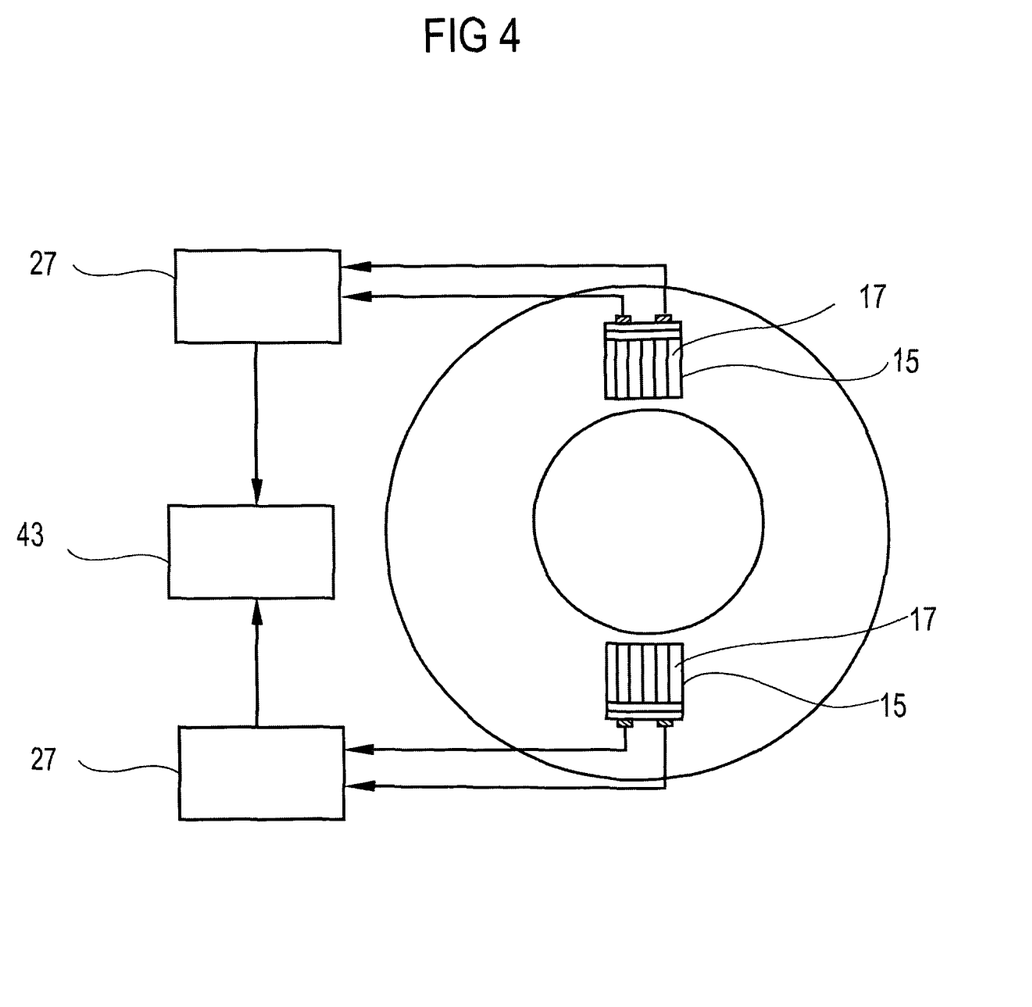
FIG. 4 illustrates an exemplary emission tomography scanner according to an embodiment herein.

Referring now to FIG. 4, an exemplary emission tomography scanner 10 is illustrated according to an embodiment herein. The scintillators 17 of FIG. 2 of the detector modules 15', 15" positioned onto the ring 5, detect a pair of photons moving in opposite directions. The output of the detector modules 15', 15", via the respective signal processing unit 27 are provided to an evaluation unit 43 to evaluate the output of the detector modules 15' and 15". The evaluation unit 43 is adapted to detect a coincidence event of the pair of the photon. The coincidence event may serve to identify a line of coincidence between the two detector modules 15', 15" positioned oppositely. The line of coincidence is a line connecting the two detector modules 15', 15".

Advantageously, the evaluation unit 43 may determine a segment on the line of coincidence, the segment being indicative for the origin of the pair of photons. The segment may be determined using a time difference of incidence of the photon pair on the two detector modules 15', 15". The increased timing resolution of the detector modules 15', 15" as per the embodiments described herein enable determining the time difference of incidence of the photon pair. This enables determining a time of flight of the respective photons of the photon pair, and thus, the segment on the line of coincidence. This enables in localizing the coincidence event to the segment on the line of coincidence.

The evaluation unit 43 can take the form of an entirely hardware embodiment, an entirely software embodiment or an embodiment including both hardware and software elements. The embodiments that are implemented in software include, but are not limited to, firmware, resident software, microcode, etc.

Furthermore, the evaluation unit 43 herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Figure 5:
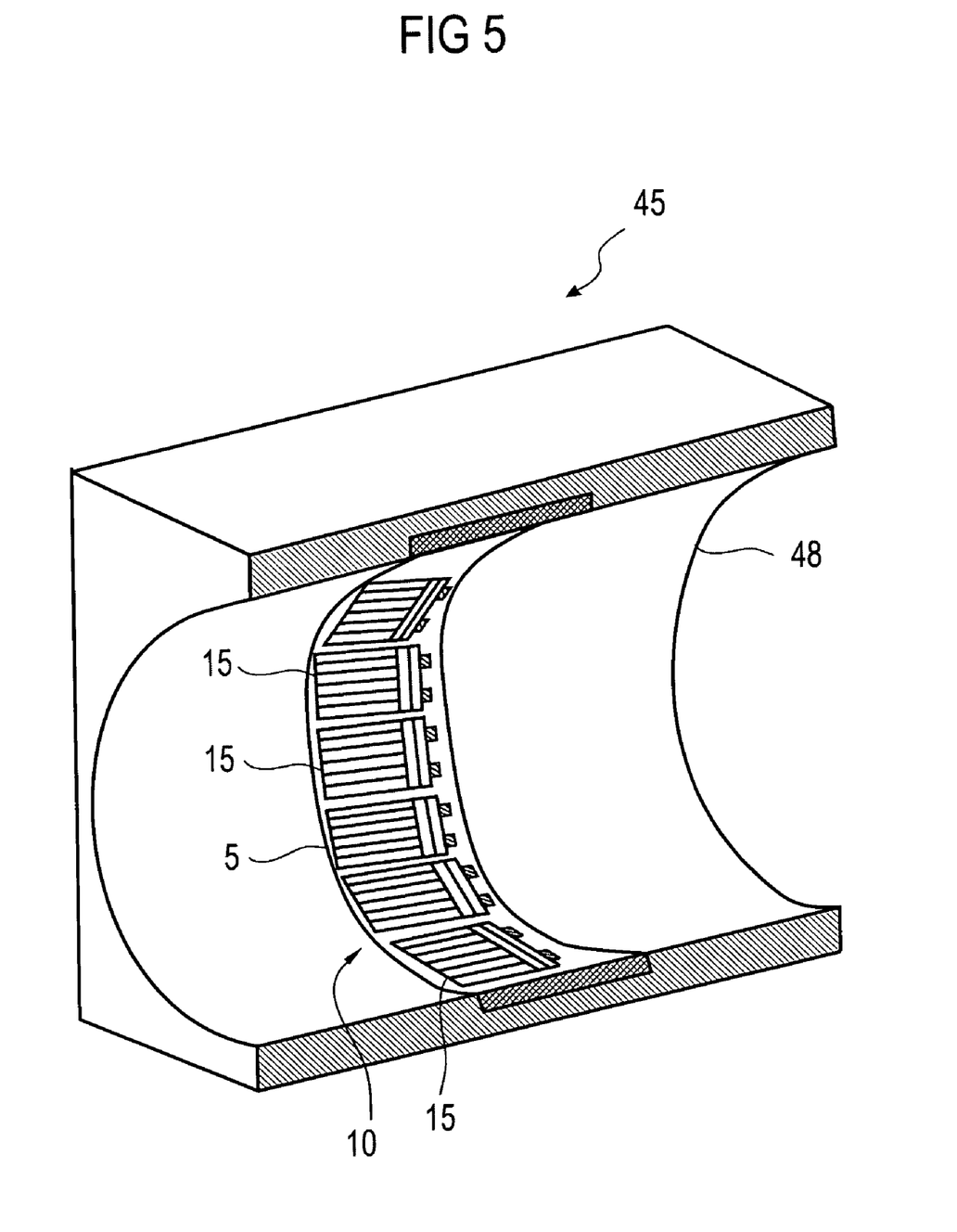
FIG. 5 illustrates an apparatus comprising an emission tomography scanner and a MRI scanner according to an embodiment herein.

FIG. 5 illustrates an apparatus comprising an emission tomography scanner 10 and a MRI scanner 45 according to an embodiment herein. A ring 5 of the emission tomography scanner 10 is disposed within a magnet system 48 of the MRI scanner 45. For example, the ring 5 may be dimensioned such that the ring 5 is received within the geometry of the MRI scanner 45. A subject to be imaged is positioned into the space defined by the MRI scanner 45 and the emission tomography scanner 10. Emission tomography and MR data acquisition may be carried out on the subject, either, simultaneously, in an interlaced or interleaved manner, or sequentially. As illustrated in the present example, the detector modules 15 of the emission tomography scanner 10 in accordance with the embodiments described herein may be arranged within the magnetic field of the magnet system 48. The first type of solid-state photodetector 21 FIG. 2 and the second type of solid-state photodetector 24 of FIG. 2 being solid-state photodetectors are not sensitive to the magnetic field of the magnet system 48.

Figure 6:
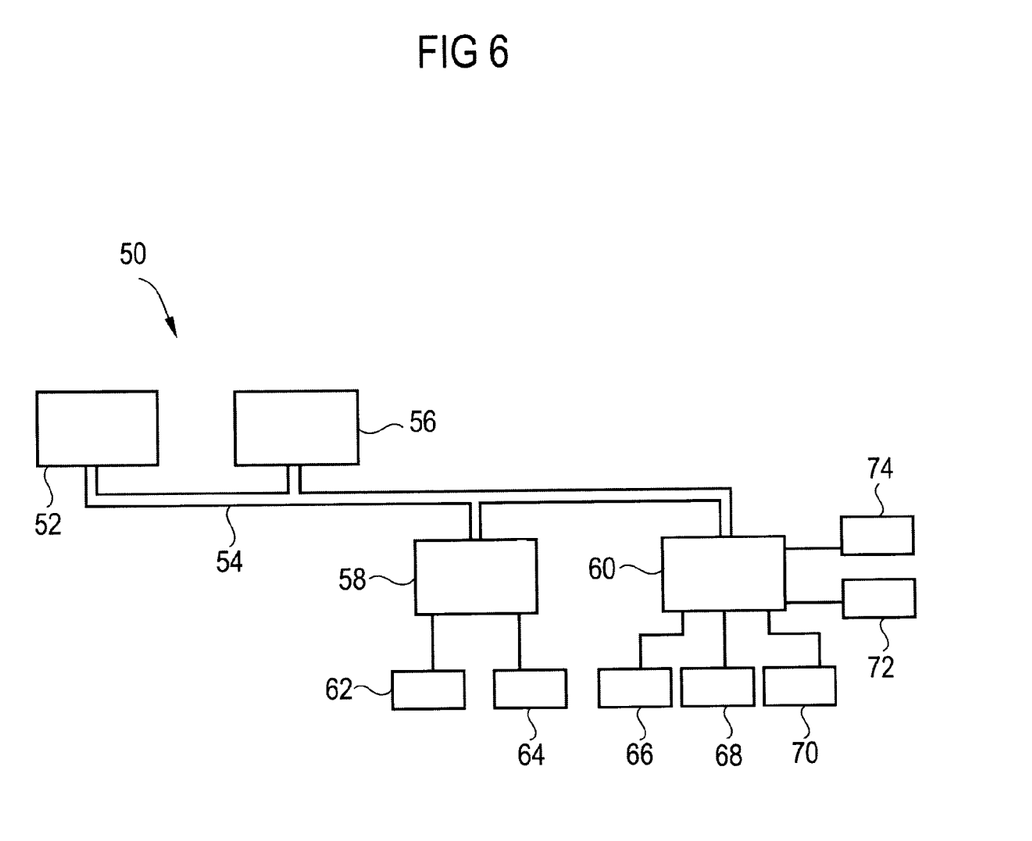
FIG. 6 illustrates a representative hardware environment for practicing the embodiments described herein.

FIG. 6 depicts a representative hardware environment for practicing the embodiments described herein. This schematic drawing illustrates a hardware configuration of an information handling/computer system 50 in accordance with the embodiments herein. The system 50 comprises at least one processor or central processing unit (CPU) 52. The CPU 52 is interconnected via bus 54 to various devices such as a memory 56, input/output (I/O) controller 58, and user interface controller 60. Depending on the type and configuration of the system 50, the memory 56 may be volatile (such as random access memory (RAM) etc., non-volatile (read only memory (ROM), flash memory devices etc.), or a combination of the two. The memory 56 is used to store instructions and data for use by the CPU 52. The I/O controller 58 can connect to peripheral devices, such as CD drives 62 and hard drives 64, or other program storage devices that are readable by the system. Typically, an operating system for the computer system 50 as well as an application program is stored onto the hard drive 64. The operating system runs on the CPU 52 and is used to coordinate and provide control of various components within system 50. The system 50 can read the inventive instructions on the hard drive 64 and load them onto the memory 56 for execution by the CPU 52. The user interface controller 60 can connect to a keyboard 66, mouse 68, speaker 70, microphone 72, display device 74 and/or other user interface devices such as a touch screen device (not shown) to the bus 54 to gather user input and also to provide system output to the user.

The embodiments described herein provide an emission tomography detector module having a compact design and increased energy and timing resolution. Increased energy resolution enable in accurately discriminating photons based on their energy. Increased timing resolution enable in localizing a coincidence event to a segment on a line of coincidence, allowing implementing a so called time of flight reconstruction mode emission tomography. Localizing a coincidence event to a segment facilitates in better image reconstruction of an image from the data acquired. Additionally, combining the output of a first type of a solid-state photodetector and a second type of solid-state photodetector to produce a combined output signal being indicative for the photon captured by the scintillator enables in reducing the number of connections required for obtaining an output of the detector module.

While this invention has been described in detail with reference to certain preferred embodiments, it should be appreciated that the present invention is not limited to those precise embodiments. Rather, in view of the present disclosure which describes the current best mode for practicing the invention, many modifications and variations would present themselves, to those of skill in the art without departing from the scope and spirit of this invention. The scope of the invention is, therefore, indicated by the following claims rather than by the foregoing description. All changes, modifications, and variations coming within the meaning and range of equivalency of the claims are to be considered within their scope.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An emission tomography detector module, comprising:
    a scintillator to capture a photon, the scintillator emitting a scintillating light upon capturing the photon;
    a first type of solid-state photodetector to detect the emitted scintillating light; and
    a second type of solid-state photodetector to detect the emitted scintillating light, the first type of solid-state photodetector and the second type of solid-state photodetector being different with respect to a detecting property.

2. The emission tomography detector module according to claim 1, wherein the detecting property is a frequency response characteristic.

3. The emission tomography detector module according to claim 1, wherein the first type of solid-state photodetector is an avalanche photodiode.

4. The emission tomography detector module according to claim 1, wherein the second type of solid-state photodetector is a silicon photomultiplier.

5. The emission tomography detector module according to claim 1, wherein the first type of solid-state photodetector and the second type of solid-state photodetector are optically coupled to the scintillator.

6. The emission tomography detector module according to claim 1, further comprising:
    a signal processing unit to combine an output signal of the first type of solid-state photodetector and an output signal of the second type of solid-state photodetector to form a combined output signal, the combined output signal being indicative for the photon captured by the scintillator.

7. The emission tomography detector module according to claim 6, wherein the output signal of the first type of solid-state photodetector is used to discriminate photons based on their energy.

8. The emission tomography detector module according to claim 6, wherein the output signal of the second type of solid-state photodetector is used for determining an incidence time of the photon.

9. The emission tomography detector module according to claim 1, further comprising:
    a plurality of the first type of solid-state photodetectors, arranged around the second type of solid-state photodetector.

10. An emission tomography scanner, comprising:
    a pair of emission tomography detector modules, each of the pair of emission tomography detector modules including
        a scintillator to capture a photon, the scintillator emitting a scintillating light upon capturing the photon;
        a first type of solid-state photodetector to detect the emitted scintillating light; and
        a second type of solid-state photodetector to detect the emitted scintillating light, the first type of solid-state photodetector and the second type of solid-state photodetector being different with respect to a detecting property.

11. The emission tomography scanner according to claim 10, wherein the detecting property is a frequency response characteristic.

12. The emission tomography scanner according to claim 10, further comprising:
    an evaluation unit to evaluate signals from the pair of emission tomography detector modules, the evaluation unit being adapted to detect a coincidence event of a pair of captured photons.

13. The emission tomography scanner according to claim 12, wherein the evaluation unit is adapted to determine a segment on a line of coincidence, the line of coincidence connecting the pair of emission tomography detector modules, wherein the segment is determined using a time difference of incidence of a photon pair on the pair of emission tomography detector modules.

14. The emission tomography scanner according to claim 10, wherein the first type of solid-state detector is an avalanche photodiode and the second type of solid-state detector is a silicon photomultiplier.

15. A combined emission tomography and magnetic resonance imaging apparatus, comprising:
a MRI scanner including a magnet system for generating a magnetic field for inducing nuclear magnetic resonance signals from nuclei of a subject to be imaged within a field of view of the MRI scanner; and
an emission tomography detector module, the emission tomography detector module including
a scintillator to capture a photon, the scintillator emitting a scintillating light upon capturing the photon;
a first type of solid-state photodetector to detect the emitted scintillating light; and
a second type of solid-state photodetector to detect the emitted scintillating light, the first type of solid-state photodetector and the second type of solid-state photodetector being different with respect to a detecting property.

16. The combined emission tomography and MRI apparatus of claim 15, wherein the emission tomography detector module is positioned within the magnetic field of the MRI scanner.

17. The combined emission tomography and MRI apparatus according to claim 15, wherein the detecting property is a frequency response characteristic.

18. The combined emission tomography and MRI apparatus according to claim 15, wherein the first type of solid-state photodetector is an avalanche photodiode and the second type of solid-state photodetector is a silicon photomultiplier.

19. The combined emission tomography and MRI apparatus according to claim 15, further comprising:
an evaluation unit to evaluate signals from a pair of the emission tomography detector modules, the evaluation unit being adapted to detect a coincidence event of a pair of photons.

20. The combined emission tomography and MRI apparatus according to claim 19, wherein the evaluation unit is adapted to determine a segment on a line of coincidence, the line of coincidence connecting the pair of emission tomography detector modules, wherein the segment is determined using a time difference of incidence of a photon pair on the pair of emission tomography detector modules.

21. The emission tomography detector module according to claim 3, wherein the second type of solid-state photodetector is a silicon photomultiplier.

22. The emission tomography detector module according to claim 7, wherein the output signal of the second type of solid-state photodetector is used for determining an incidence time of the photon.

23. The emission tomography detector module according to claim 1, wherein the first type of solid-state photodetector includes a plurality of first type of solid-state photodetectors and wherein the second type of solid-state photodetector includes a plurality of second type of solid-state photodetectors, the plurality of first type of solid-state photodetectors being arranged around the plurality of second type of solid-state photodetectors.

24. The emission tomography detector module according to claim 1, further comprising:
a plurality of the first type of solid-state photodetectors, arranged around a plurality of the second type of solid-state photodetectors.

* * * * *